US010105189B2

(12) United States Patent
Still et al.

(10) Patent No.: US 10,105,189 B2
(45) Date of Patent: Oct. 23, 2018

(54) TECHNIQUES FOR CORRECTING AN ERROR IN A NONVOLATILE MEMORY OF AN EMBEDDED COMPONENT FOR AN END EFFECTOR IN A ROBOTIC SURGICAL SYSTEM

(71) Applicant: MAKO Surgical Corp., Ft. Lauderdale, FL (US)

(72) Inventors: Stephen Eugene Still, Lake Worth, FL (US); Renbin Zhou, Wellington, FL (US)

(73) Assignee: MAKO Surgical Corp., Ft. Lauderdale, FL (US)

( * ) Notice: Subject to any disclaimer, the term of this patent is extended or adjusted under 35 U.S.C. 154(b) by 0 days.

(21) Appl. No.: 15/348,443

(22) Filed: Nov. 10, 2016

(65) Prior Publication Data

US 2017/0128142 A1    May 11, 2017

Related U.S. Application Data

(60) Provisional application No. 62/253,364, filed on Nov. 10, 2015.

(51) Int. Cl.
*A61B 34/30* (2016.01)
*B25J 9/16* (2006.01)
(Continued)

(52) U.S. Cl.
CPC .............. *A61B 34/30* (2016.02); *A61B 34/37* (2016.02); *B25J 9/1674* (2013.01);
(Continued)

(58) Field of Classification Search
CPC ......... A61B 34/30; A61B 34/37; A61B 17/00; A61B 2017/00477; A61B 2034/306;
(Continued)

(56) References Cited

U.S. PATENT DOCUMENTS 4,912,708 A    3/1990 Wendt
5,793,943 A    8/1998 Noll
(Continued)

OTHER PUBLICATIONS

Jim Cooke, "Micron.RTM. e-MMC.TM. Embedded Memory Simplifies High-Capacity Storage for Mobile and Embedded Systems," pp. 1-7, 2007 Micron Technology, Inc.*

*Primary Examiner* — Cynthia Britt
(74) *Attorney, Agent, or Firm* — Howard & Howard Attorneys PLLC

(57) ABSTRACT

A method for correcting an error of a nonvolatile memory of an embedded component for an end effector used in a robotic surgical system is provided. The robotic surgical system includes a host controller in communication with the embedded component. The embedded component of the end effector performs a test process to test the nonvolatile memory. The host controller of the robotic surgical system requests a result of the test process from the embedded component of the end effector. The host controller determines that the error of the nonvolatile memory has occurred after requesting the result of the test process from the embedded component of the end effector. The host controller modifies the nonvolatile memory of the embedded component of the end effector to correct the error.

18 Claims, 7 Drawing Sheets

(51) Int. Cl.
*A61B 34/37* (2016.01)
*B25J 15/00* (2006.01)
*G11C 29/08* (2006.01)
*G06F 11/22* (2006.01)
*G11C 16/34* (2006.01)
*A61B 17/00* (2006.01)

(52) U.S. Cl.
CPC ....... *B25J 15/0019* (2013.01); *G06F 11/2284* (2013.01); *G11C 16/3459* (2013.01); *G11C 29/08* (2013.01); *A61B 17/00* (2013.01); *A61B 2017/00477* (2013.01); *A61B 2034/306* (2016.02); *Y10S 901/01* (2013.01); *Y10S 901/41* (2013.01)

(58) Field of Classification Search
CPC ...... B25J 34/37; B25J 15/0019; B25J 9/1674; G11C 29/36; G11C 29/38; G11C 29/4401; G11C 29/00; G11C 16/3459; G11C 29/08; G11C 29/42; G01R 31/282; Y10S 901/01; Y10S 901/41; G06F 11/1008; G06F 1/1666; G06F 11/2284
See application file for complete search history.

(56) References Cited

U.S. PATENT DOCUMENTS

| | | | |
|---|---|---|---|
| 5,805,882 | A | 9/1998 | Cooper et al. |
| 6,915,417 | B2 | 7/2005 | Stein et al. |
| 7,069,431 | B2 | 6/2006 | Dayan et al. |
| 7,100,087 | B2 | 8/2006 | Yang et al. |
| 7,111,159 | B2 | 9/2006 | Stein et al. |
| 7,185,191 | B2 | 2/2007 | Bosley et al. |
| 7,529,921 | B2 | 5/2009 | Stein et al. |
| 7,571,352 | B2 | 8/2009 | Weichselbaum |
| 7,730,362 | B2 | 6/2010 | Claus et al. |
| 7,962,795 | B2 | 6/2011 | Kwon |
| 8,312,098 | B2 | 11/2012 | Claus et al. |
| 8,595,608 | B2 | 11/2013 | Nolte |
| 8,645,776 | B2 * | 2/2014 | Byom .................... G11C 29/42 714/723 |
| 8,775,877 | B2 | 7/2014 | McVey et al. |
| 9,092,552 | B2 | 7/2015 | Nair et al. |
| 2002/0049950 | A1 * | 4/2002 | Loaiza ................ G06F 11/1004 714/763 |
| 2003/0056145 | A1 | 3/2003 | Kuth |
| 2003/0140288 | A1 * | 7/2003 | Loaiza ................ G06F 11/0727 714/718 |
| 2003/0204797 | A1 * | 10/2003 | Lin ........................ G11C 29/48 714/718 |
| 2010/0313105 | A1 | 12/2010 | Nekoomaram et al. |
| 2011/0239064 | A1 * | 9/2011 | Byom ................ G06F 11/1048 714/723 |
| 2013/0080757 | A1 | 3/2013 | Chou |
| 2014/0157065 | A1 * | 6/2014 | Ong ....................... G11C 29/12 714/718 |
| 2014/0325287 | A1 | 10/2014 | Nair et al. |
| 2014/0380104 | A1 | 12/2014 | Lee et al. |
| 2015/0355965 | A1 * | 12/2015 | Peddle .................... G06F 13/28 714/773 |
| 2016/0012918 | A1 * | 1/2016 | Mun .................... G11C 29/789 714/718 |

\* cited by examiner

TECHNIQUES FOR CORRECTING AN ERROR IN A NONVOLATILE MEMORY OF AN EMBEDDED COMPONENT FOR AN END EFFECTOR IN A ROBOTIC SURGICAL SYSTEM

CROSS REFERENCE TO RELATED APPLICATION

The subject application claims the benefit of U.S. Provisional Patent Application No. 62/253,364, filed on Nov. 10, 2015, the contents of which are incorporated by reference in their entirety.

TECHNICAL FIELD

The subject invention relates to a method for detecting and recovering from a memory error of an embedded component of an end effector used in a robotic surgical system.

BACKGROUND

Accurate and reliable methods of memory error detection and recovery are becoming increasingly necessary as robotic surgical technology expands. Memory errors are often caused in nonvolatile memory of end effectors of robotic surgical systems by elevated temperatures such as those produced by an autoclave during sterilization of an end effector. In sensitive applications, such as robotic surgical systems, memory errors can cause malfunction of the robotic surgical systems. Malfunction of the robotic surgical system during surgery can have severe health-related and financial consequences for patients, surgeons, and hospitals. Furthermore, when such memory errors occur in end effectors, the error is typically addressed using manual human intervention thereby causing inconvenience for end users and prolonged lack of operability of the robotic surgical system. As such, there is a need to address at least the aforementioned problems.

SUMMARY AND ADVANTAGES

One embodiment of a method for correcting an error of a nonvolatile memory of an embedded component for an end effector used in a robotic surgical system is provided. The robotic surgical system includes a host controller in communication with the embedded component. The embedded component of the end effector performs a test process to test the nonvolatile memory. The host controller of the robotic surgical system requests a result of the test process from the embedded component of the end effector. The host controller determines that the error of the nonvolatile memory has occurred after requesting the result of the test process from the embedded component of the end effector. The host controller modifies the nonvolatile memory of the embedded component of the end effector to correct the error.

One embodiment of a host controller of a robotic surgical system is provided. The host controller is configured to communicate with an embedded component of an end effector used in the robotic surgical system. The embedded component comprises a nonvolatile memory. The host controller is configured to request a result of a test process related to the nonvolatile memory from the embedded component of the end effector. The host controller is configured to determine that an error has occurred in the nonvolatile memory of the embedded component after requesting the result of the test process. The host controller modifies the nonvolatile memory of the embedded component of the end effector to correct the error.

One embodiment of an end effector for use in a robotic surgical system is provided. The end effector is configured to communicate with a host controller of the robotic surgical system. The end effector comprises an embedded component comprising a nonvolatile memory. The embedded component is configured to perform a test process to test the nonvolatile memory. The embedded component is configured to report a result of the test process to the host controller of the robotic surgical system. The embedded component allows modification of the nonvolatile memory by the host controller to correct an error in the nonvolatile memory determined based on the result of the test process.

The techniques advantageously provide accurate and reliable detection of and recovery from a memory error, such as those memory errors caused by an autoclave during sterilization of the end effector. The host controller initiates a test of the nonvolatile memory of the embedded component of the end effector. If the results of the test process are indicative of a memory error, or if the embedded component fails to respond, the host controller remedies the memory error. Therefore, the techniques accurately and reliably prevent severe consequences caused by malfunction of the robotic surgical system during surgery. This allows the method to be employed in sensitive applications where accurately and reliably detecting and recovering from memory errors is critical to avoid health-related and financial consequences of robotic surgery and to comply with safety regulations, and the like. Furthermore, the techniques identify and correct the error automatically and without the need for human intervention to correct the error, thereby increasing convenience for end users and operability of the robotic surgical system. Those skilled in the art appreciate that the techniques described herein may exhibit advantages other than those described above.

DETAILED DESCRIPTION

Referring to the Figures, wherein like numerals indicate like or corresponding parts throughout the several views, aspects of a robotic surgical system 10 and steps of a method 40a, 40b for detecting and recovering from (i.e., correcting) a memory error of a nonvolatile memory of an embedded component of an end effector used in the robotic surgical system 10 are provided.

Figure 1:
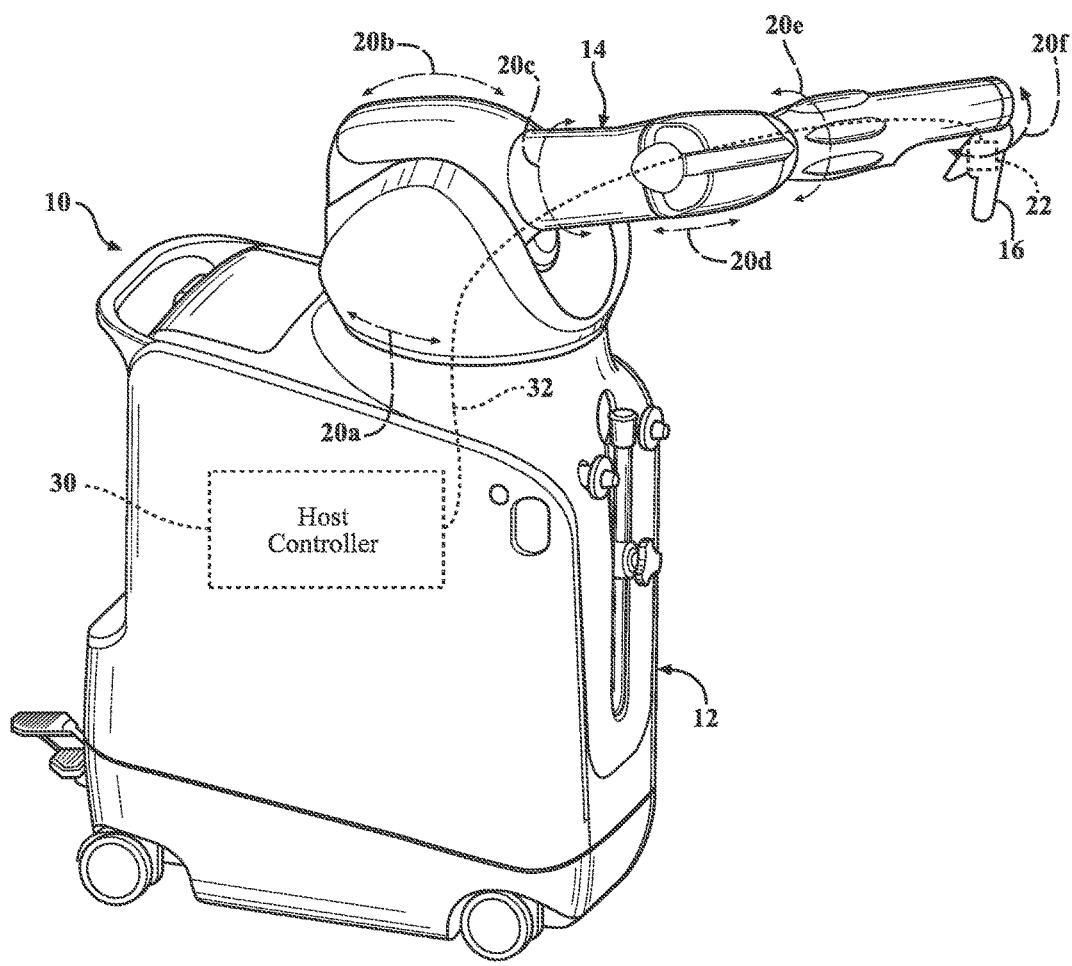
FIG. 1 is a perspective view of a robotic surgical system for performing robotic or robot-assisted surgery illustrating an end effector including an embedded component and a host controller in communication with the end effector, according to one embodiment.

FIG. 1 illustrates an exemplary embodiment of the robotic surgical system 10. The robotic surgical system 10 includes a base (or cart) 12 and an arm 14 extending from the base 12. An end effector 16 is disposed on an end of the arm 14. The end effector 16 is designed to perform various surgical tasks, such as but not limited to ablating, cutting, sensing, suctioning, illuminating, grasping, manipulating, and suturing. In one embodiment, the end effector 16 may include a bur for removing tissue. In another example, the end effector 16 may include a suctioning device and a sensor for sensing and suctioning excess fluids from a wound of a patient. In other examples, the end effector 16 may include a light source, a manipulator, an ultrasonic device, a suturing device, a scalpel, a sagittal saw, or any other device suitable for use by a robotic surgical system 10. In some embodiments, the end effector 16 has an actuator, such as a motor. The actuator drives a part of the end effector 16 that moves, such as a bur, a suctioning device, a manipulator, a suturing device, a sagittal saw, or any other suitable device that requires a driving force to operate. Those skilled in the art appreciate that the end effector 16 may have configurations other than those specifically described herein.

Figure 2:
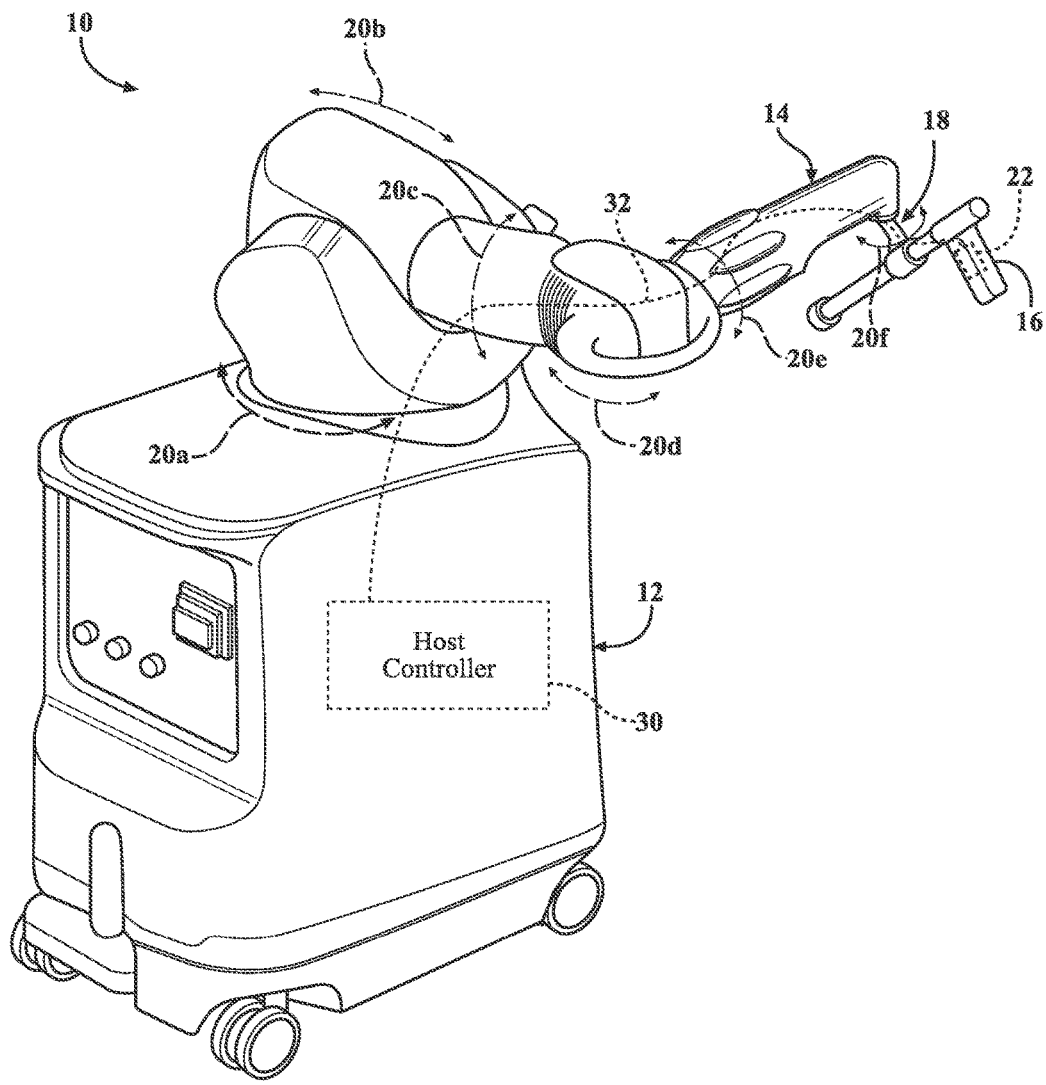
FIG. 2 is a perspective view of the robotic surgical system further illustrating a coupling device for supporting the end effector, according to one embodiment.
Figure 4:
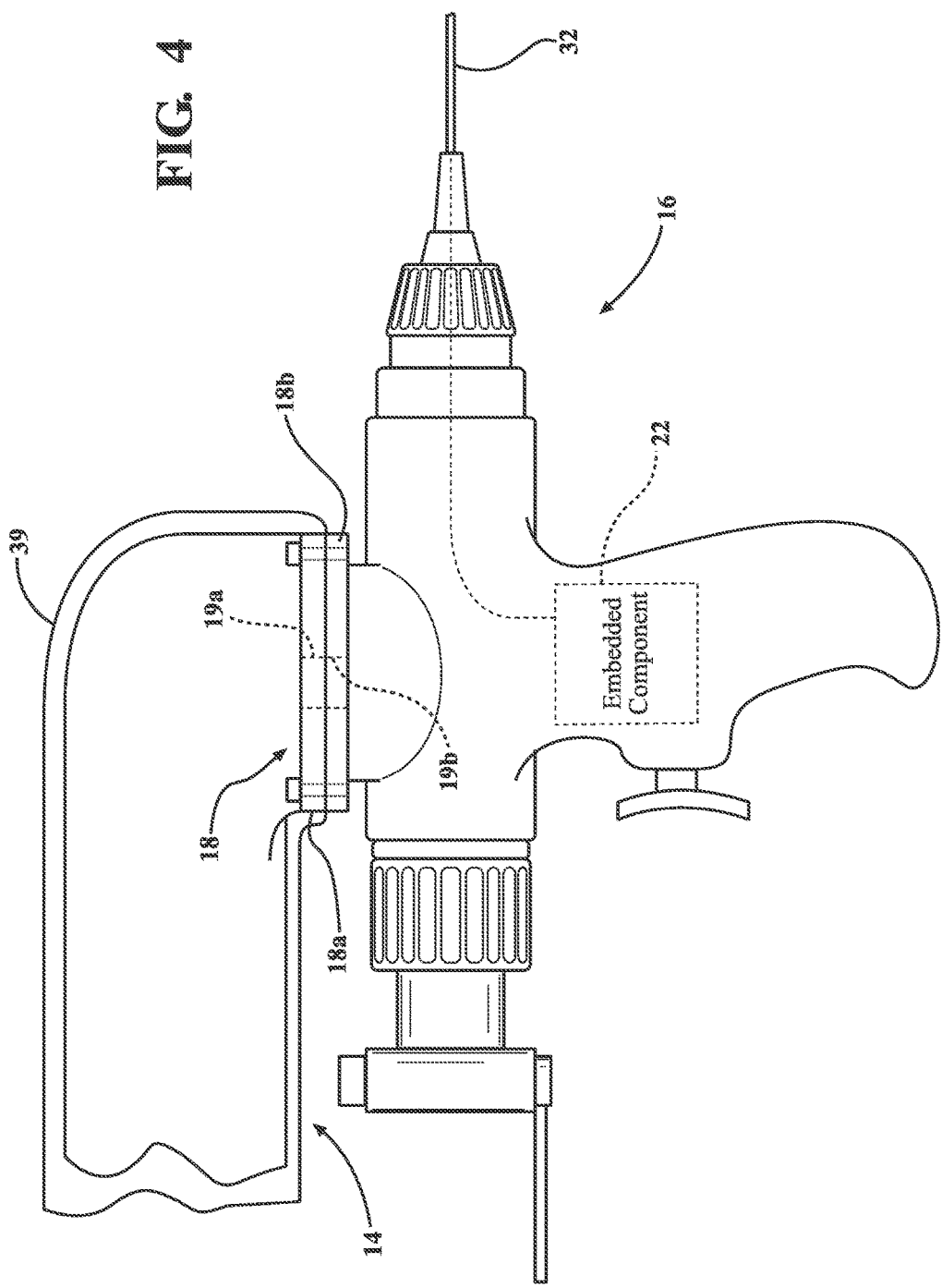
FIG. 4 is a schematic illustration of a connection between the end effector and a robotic arm of the robotic surgical system, according to one embodiment.

In some embodiments, as shown in FIGS. 2 and 4, the end effector 16 is disposed on the end of the arm 14 by a coupling device 18. The coupling device 18 allows a surgeon or a surgical technologist to attach the end effector 16 to the robot or detach the end effector 16 from the robotic surgical system 10 such that the surgeon can interchange different end effectors 16 as is necessary for a surgical operation. For example, the surgeon can use the coupling device 18 to quickly and easily decouple a burring end effector 16 from the robotic surgical system 10 and replace it with an ablating end effector 16.

In the embodiment shown in FIG. 4, the arm 14 comprises a first mounting portion, such as a mounting flange 18a disposed at a distal end of the arm 14. The coupling device 18 comprises a second mounting portion that forms part of the end effector 16, such as a complimentary mounting flange 18b. The mounting portions, e.g., the mounting flanges 18a, 18b, are configured to be connected together, such as by fasteners, snap-fit connections, magnetic coupling, and the like. Electrical connectors 19a, 19b may also be present on the mounting portions. The electrical connectors 19a, 19b may be configured to engage one another when mounting the end effector 16 to the robot arm 14 for purposes of establishing communication (e.g., data, power, or other electrical communication) between the robot arm 14 and the end effector 16 for the purposes described herein. The electrical connectors 19a, 19b may provide electrical pin connections to provide communication or may be components utilized in wireless communication, e.g., radio frequency, infrared, or other types of wireless communication components.

Figure 3:
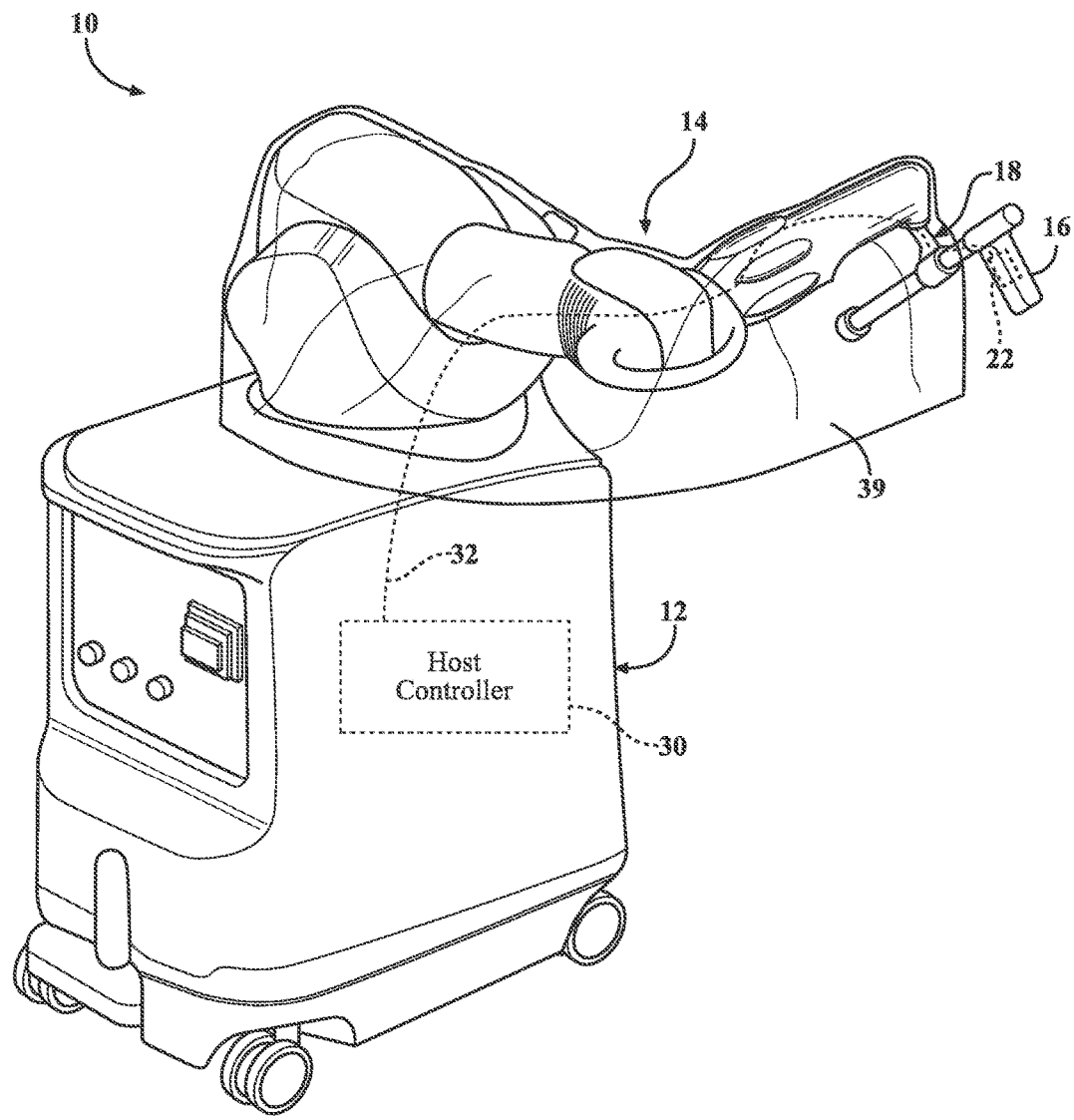
FIG. 3 is a perspective view of the robotic surgical system further illustrating a sterile drape covering the end effector, according to one embodiment.

In some embodiments, the arm 14 has a plurality of joints 20a, 20b, 20c, 20d, 20e, 20f. Each joint 20a, 20b, 20c, 20d, 20e, 20f is illustrated in the Figures by an arrow showing motion of the joint. Each joint 20a, 20b, 20c, 20d, 20e, 20f allows the arm 14 to move or be moved in at least one degree of freedom. In some embodiments, the joints 20a, 20b, 20c, 20d, 20e, 20f allow the arm 14 to be translated, rotated, or a combination thereof, thereby allowing the arm 14 to position the end effector 16. The arm 14 may have a serial arm configuration, such as shown in FIGS. 1-3. Alternatively, the arm 14 may have other configurations, such as a parallel arm configuration, or the like.

In some embodiments, the arm 14 has a plurality of joint motors each being associated with one or more of the joints 20a, 20b, 20c, 20d, 20e, 20f to move the arm 14. The joint motors can be active or passive. The joint motors that are active move at least a portion of the arm 14 in response to electrically signaled instructions such that the end effector 16 is positioned according to circumstances of surgery being performed. The electrically signaled instructions can be determined during pre-surgical planning, can be determined by the surgeon or the surgical technologist during surgery, such as by a control interface, or can be determined by any other suitable means. The joint motors that are passive respond to forces applied by the surgeon to the end effector 16. In other words, the surgeon can apply force the end effector 16 in a desired direction, and the joint motors that are passive will respond as necessary such that the end effector 16 moves in the desired manner. In some embodiments, all of the joint motors are active. In other embodiments, all of the joint motors are passive. In other embodiments, some joint motors are active and other joint motors are passive. In other embodiments, the surgeon can select whether the joint motors are active or passive.

Figure 5:
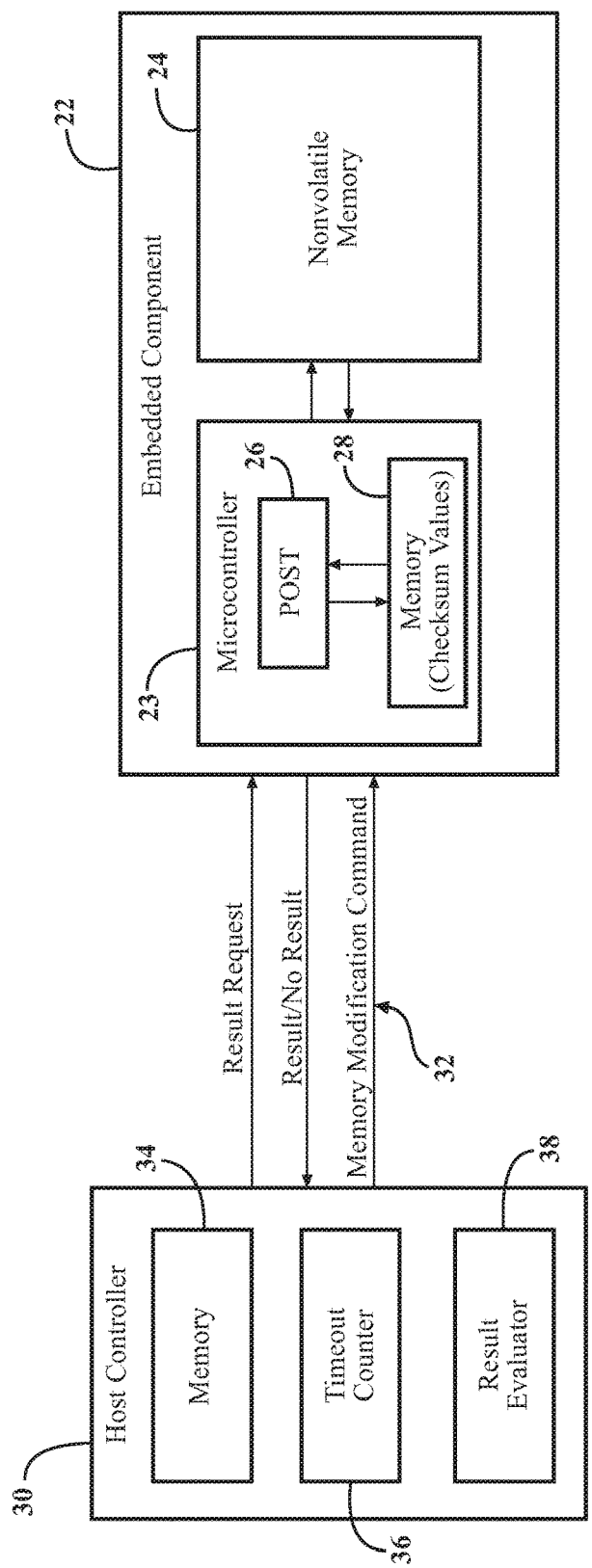
FIG. 5 is a block diagram of the host controller and the embedded component, and sub-components and sub-modules thereof, according to one embodiment.

As shown in FIGS. 4 and 5, the end effector 16 has an embedded component 22 for controlling the end effector 16. The embedded component 22 is a computer sub-system or computing device dedicated to controlling the end effector 16 or components/functions thereof. In one embodiment, as shown in FIG. 5, the embedded component 22 may include a microcontroller 23. The microcontroller 23 may be for controlling operation of the actuator for a bur of the end effector 16. In another example, the embedded component 22 (or microcontroller 23) may include an application specific integrated circuit (ASIC). The ASIC may be for controlling and calibrating a sensor of the end effector 16. Those skilled in the art appreciate that the embedded component 22 may have configurations other than those specifically described herein.

The embedded component 22 has a nonvolatile memory 24. The term "nonvolatile memory" is used to described a type of computer memory that is configured to hold saved data stored thereon even after the embedded component 22 and/or nonvolatile memory 24 is cycled (powered) off and back on. As such, the nonvolatile memory 24 is used as secondary storage, or long-term persistent storage. Nonvolatile memory 24 is distinguished from volatile memory, which does not hold data stored thereon after it is cycled off and back on, causing the data to be lost. In one example, the nonvolatile memory 24 stores information such as programs and processes for operating the end effector 16, and calibration data, usage data, and/or identification data for the end effector 16. In one embodiment, the nonvolatile memory 24 is read-only memory (ROM). For example, the nonvolatile memory 24 can be electrically erasable programmable read-only memory (EEPROM), such as flash memory. The nonvolatile memory 24 and the microcontroller 23 may be incorporated on a common printed circuited board (PCB) of the embedded component 22. The microcontroller 23 communicates with the nonvolatile memory 24 for purposes related to reading and writing data from the nonvolatile memory 24, and the like. Those skilled in the art appreciate that the nonvolatile memory 24 may have configurations other than those specifically described herein.

As shown in FIG. 5, the embedded component 22 comprises computer executable instructions (or a module) for implementing a POST 26, which is a power on self test (also referred to herein as a "test process"). The POST 26 may be stored on a memory component 28 of the embedded component 22 or the microcontroller 23. The embedded component 22 may include, or be coupled to, one or more processors for executing computer readable instructions of the POST 26. The memory component 28 may be any suitable type of memory, such as programmable read-only memory (PROM), erasable programmable read-only memory (EPROM), EEPROM, such as flash memory, or the like. The POST 26 is configured to be executed upon powering on (booting up) of the end effector 16, or more specifically, the embedded component 22. In one example, the POST 26 is a diagnostic test that is executed to determine if the nonvolatile memory 24 is operating correctly or has errors. As described below, one example of this diagnostic test is a checksum test performed in relation to the nonvolatile memory 24.

As shown in FIGS. 4 and 5, the robotic surgical system 10 has a host controller 30. In one embodiment, the host controller 30 is located within the base 12 or the cart of the robotic surgical system 10. The host controller 30 is a computer system, such as a microcontroller or an ASIC. The host controller 30 can be any computer system suitable for controlling some functions of the robotic surgical system 10. The host controller 30 may be for controlling the arm 14, surgical sensors, other components of the robotic surgical system 10, or a combination thereof. The host controller 30 is a primary controller configured to send commands to the embedded component 22. In some embodiments, the host controller 30 is a master controller and the microcontroller 23 of the embedded component 22 is a slave controller. In some embodiments, the host controller 30 controls the actuator of the end effector 16. In some embodiments, the host controller 30 controls the joint motors. The joint motors can connect to the host controller 30 in series or in parallel. Those of skill in the art appreciate that the host controller 30 can control any suitable electrically controlled aspect of the robotic surgical system 10.

A data connection 32 connects the embedded component 22 and the host controller 30. The data connection 32 allows exchange of data between the embedded component 22 and the host controller 30. In some embodiments, the data connection 32 is a wired connection, such as a wired serial connection. When wired, the data connection 32 may pass through the arm 14 of the robotic surgical system 10, as shown in FIGS. 1-3. In such embodiments, the data connection 32 may pass through the electrical connectors 19a, 19b as shown in FIG. 4. In another embodiment, as shown in FIG. 4, the data connection 32 may be wired externally to the end effector 16 thereby bypassing the arm 14. The end effector 16 may comprise any suitable connection for connecting to the data connection 32. In other embodiments, the data connection 32 is a wireless connection. The data connection 32 may allow data transmission according to any suitable communication protocol. The data connection 32 may also be a data bus.

The host controller 30 may comprise or be coupled to a host memory 34. The host memory 34 is a computer memory for storing an image, i.e. copy, of the nonvolatile memory 24 of the embedded component 22. The host memory 34 can be dedicated to the storing of the image of the nonvolatile memory 24, or can be a portion of general purpose memory of the host controller 30. The host memory 34 may also store results of the POST 26 received from the embedded component 22. In one embodiment, the host memory 34 is ROM. For example, the host memory 34 can be programmable read-only memory (PROM), erasable programmable read-only memory (EPROM), or EEPROM, such as flash memory. Those skilled in the art appreciate that the host memory 34 may have configurations other than those specifically described herein.

As shown in FIG. 5, the host controller 30 also implements a timeout counter 36. The timeout counter 36, which is run by an internal clock, is triggered upon the host controller 30 requesting the result of the POST 26 from the embedded component 22. As is described below, the host controller 30 waits to see if the result of the POST 26 is received within a predetermined period of time after triggering of the timeout counter 36, for error detection purposes. The timeout counter 36 may be implemented according to any suitable technique and the predetermined period may be of any suitable duration.

A result evaluator 38 is also implemented by the host controller 30. The result evaluator 38 may include computer readable instructions that, when executed, are configured to evaluate or analyze the result of the POST 26 received from the embedded component 22. The result evaluator 38 may be coupled to the timeout counter 36 to determine whether the result of the POST 26 is received from the embedded component 22. If and when the result of the POST 26 is received, the result evaluator 38 is configured to determine or identify what specific error(s) occurred in the nonvolatile memory 24. The result evaluator 38 is also configured to generate a memory modification command commensurate with the identified error(s) and transmit the same to the embedded component 22, and more specifically, the nonvolatile memory 24 for correction of such errors. The host controller 30 is configured to perform such functions in an automated fashion such that no direct human intervention is needed to perform the same. The result evaluator 38 may be implemented according to any suitable technique and may perform other functions not specifically described herein related to error detection and recovery.

In some embodiments, the end effector 16 is sterilized. The arm 14 may or may not be sterilized. FIG. 3 illustrates the sterilized end effector 16 and the coupling device 18 separated from the arm 14 by a drape 39. The drape 39 is placed between the end effector 16 and the arm 14 such that the sterilized end effector 16 and the patient are separated from the unsterile arm 14. In other embodiments, the unsterile arm 14 is enclosed by a surgical wrap such that the unsterile arm 14 is separated from the sterile end effector 16. In some embodiments, the coupling device 18 is sterilized. The sterile coupling device 18 is also separated from the unsterile arm 14 by the drape 39 or the surgical wrap.

In some embodiments, the end effector 16 is sterilized using an autoclave (not shown). The autoclave sterilizes the end effector 16 by exposing the end effector 16 to high temperatures. Exposure to high temperatures can cause memory errors, such as bit errors, in the nonvolatile memory 24 of the end effector 16. Memory errors can negatively affect performance of the end effector 16. For example, a memory error can alter a calibration value in the nonvolatile memory 24, thereby causing a bur of the end effector 16 to operate too quickly, too slowly, or not at all. In another example, a memory error can alter one or more bits of a program code that allows the end effector 16 to function. The memory error can thereby cause the end effector 16 to be unable to function, to function erratically, or to otherwise malfunction. Examples of such memory errors include undesired alteration of bits and/or corruption of data stored on the nonvolatile memory 24.

Figure 6:
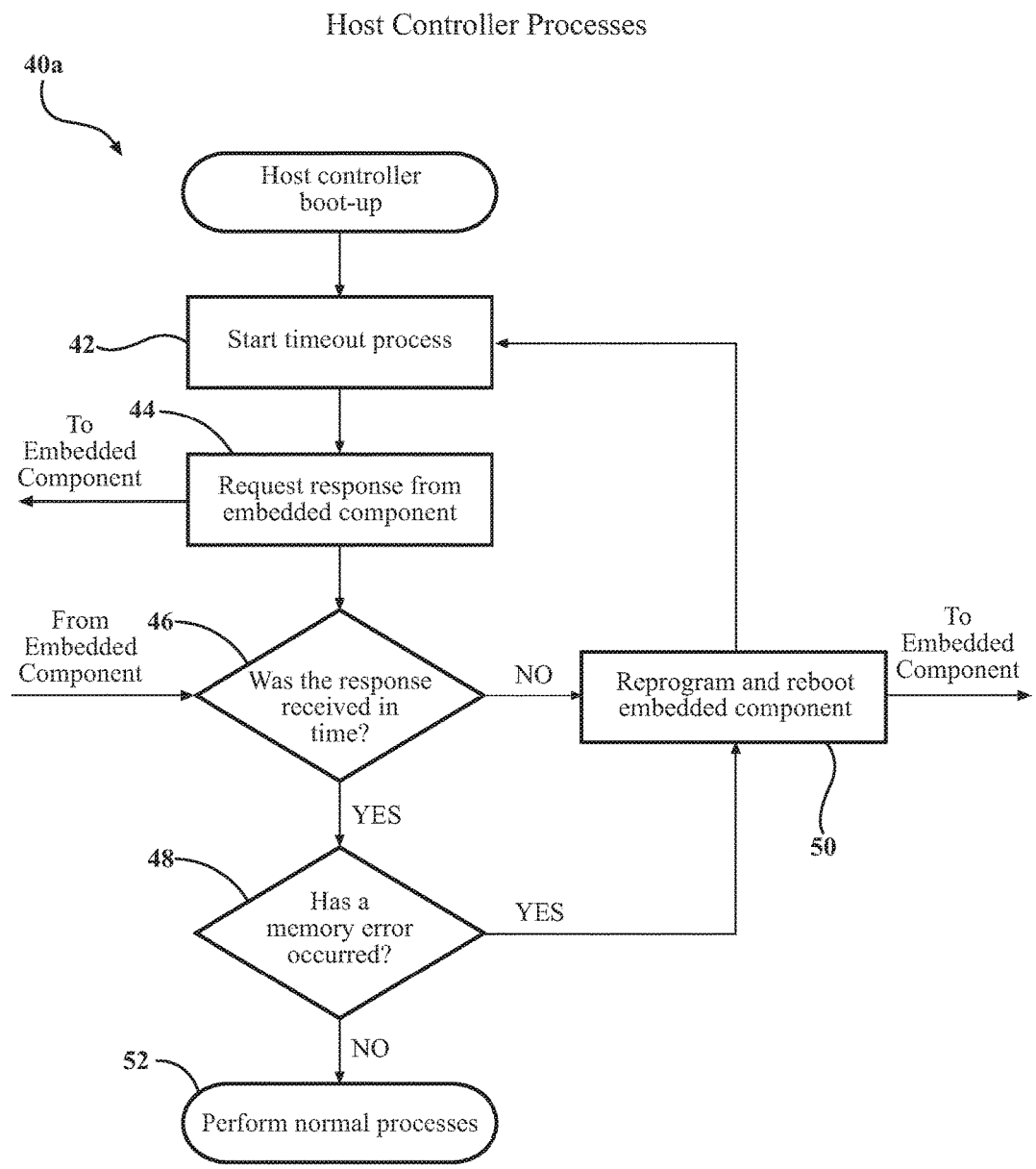
FIG. 6 is one embodiment of a flowchart of steps performed by the host controller relating to detecting and recovering from an error of a nonvolatile memory of the embedded component of the end effector.
Figure 7:
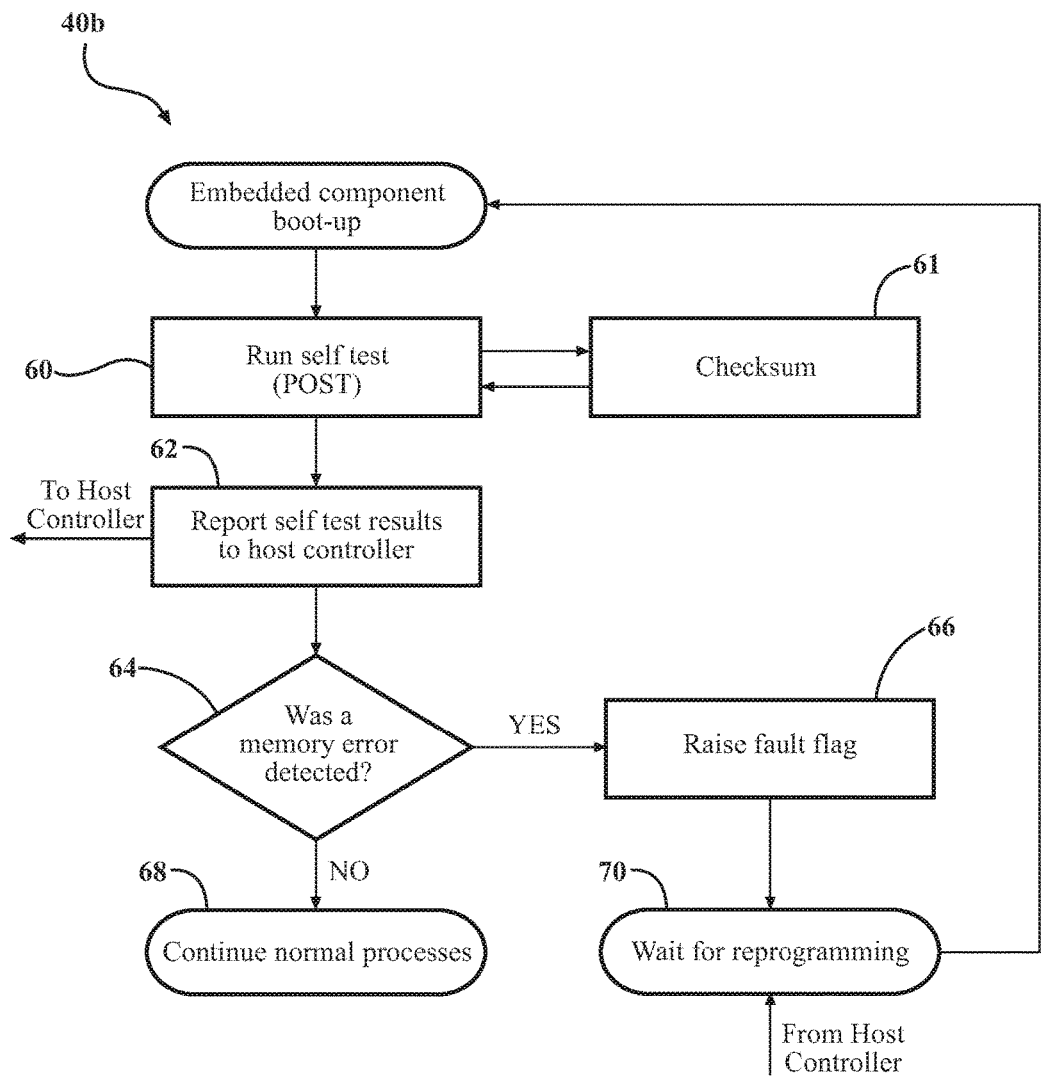
FIG. 7 is one embodiment of a flowchart of steps performed by the embedded component relating to detecting and recovering from the error of the nonvolatile memory of the embedded component of the end effector.

FIGS. 6 and 7 are flowcharts illustrating methods 40a, 40b for detecting and recovering from (i.e., correcting) the memory error of the nonvolatile memory 24. FIG. 6 illustrates the method 40a performed by the host controller 30. FIG. 7 illustrates method 40b performed by the embedded component 22. Collectively, these methods 40a, 40b operate in parallel to implement the method for correcting the error. The methods 40a, 40b may be performed upon booting the embedded component 22 after attachment of the end effector 16 to the arm 14. In other embodiments, the methods 40a, 40b are performed after booting up the robotic surgical system 10, generally. In some embodiments, the method 40b performed by the embedded component 22 is performed upon booting the embedded component 22 after the embedded component 22 has been sterilized. The methods 40a, 40b may be performed or initiated synchronously or asynchronously depending upon the situation.

Referring to FIG. 6, after the host controller 30 is booted up, the host controller 30 starts a timeout process at step 42. The timeout process includes starting the timeout counter 36. The timeout counter 36 is set to elapse after the predetermined timeout time. The timeout time is set such that the embedded component 22 has at least enough time to perform the POST 26 and communicate a result of the POST 26 to the host controller 30 before the predetermined timeout time elapses. In one example, the predetermined timeout time is greater than 3 seconds and less than 30 seconds. Other suitable timeout times may be utilized. As is described in detail below, the result of the POST 26 is indicative of whether the memory error has occurred in the nonvolatile memory 24.

At step 44 the host controller 30 requests a response from the embedded component 22. As shown in FIG. 5, the request is sent from the host controller 30 to the embedded component 22 through the data connection 32. The requested response sought by the host controller 30 is the result of the POST 26. Steps 42 and 44 may occur simultaneously, or nearly simultaneously, such as within 0.1 seconds of each other. As such, the timeout counter 36 is running before or at the time the request for the response is sent to the embedded component 22.

At step 46, the host controller 30 awaits the result of the POST 26 from the embedded component 22. The host controller 30, in conjunction with the timeout counter 36, determines whether the result of the POST 26 was received in time, i.e., whether the result was received before lapsing of the predetermined timeout time set by the timeout counter 36. The host controller 30 performs step 46 to determine whether the embedded component 22 is able to complete the POST 26. If the POST 26 is not completed by the embedded component 22, the result evaluator 38 can determine that the embedded component 22 was unable to complete the POST 26 due to an error or malfunction, such as an error or malfunction in the nonvolatile memory 24. In such instances, the outcome of step 46 is "NO" in that the response from the embedded component 22 was not received in time, and the method 40a proceeds to step 50, described below.

If, however, the result of the POST 26 was received by the host controller 30, this indicates to the result evaluator 38 that indeed the POST 26 was completed by the embedded component 22. If the response was received, the outcome of step 46 is "YES" in that the response from the embedded component 22 was received in time, and the method 40a proceeds to step 48, described below.

At step 48 the host controller 30, and more specifically, the result evaluator 38, reads and/or analyzes the result of the POST 26 to determine whether the result indicates that the error has occurred in the nonvolatile memory 24. If the response indicates to the result evaluator 38 that the error has occurred, the host controller 30 initiates step 50. If the response indicates that the error has not occurred, the host controller 30 performs normal processes (step 52). Normal processes include any process outside of the method such as, but not limited to, controlling the arm 14, analyzing surgical navigation data, interfacing with the embedded component 22 and the actuator to perform post-boot processes, like operating a bur and the like.

At step 50 the host controller 30 generates a memory modification command to modify the nonvolatile memory 24 to correct the error. In one embodiment, the host controller 30 does so by commanding a reprogram of the embedded component 22 (and nonvolatile memory 24), thereby rectifying the error. The host controller 30 may also command a rebooting of the embedded component 22 (and nonvolatile memory 24). The host controller 30 performs such reprogramming by rewriting at least a portion of the nonvolatile memory 24 with the image of the nonvolatile memory 24 stored in the host memory 34. In some embodiments, if the host controller 30 received the response (in time) during step 46, the host controller 30 will rewrite only a portion of the nonvolatile memory 24 that includes the memory error, thereby saving time, in lieu of rewriting the nonvolatile memory 24 in its entirety. In other embodiments, the host controller 30 rewrites the nonvolatile memory 24 in its entirety. The host controller 30 then reboots the embedded component 22. After completing step 50, the method 40a is restarted and the timeout process of step 42 may be re-performed depending upon a triggering event, such as reconnection of the end effector 16, rebooting of the surgical system 10, or according to a routine maintenance check schedule (e.g., once a day), and the like.

FIG. 7 illustrates the parallel method 40b performed by the embedded component 22 of the end effector 16 to correct the error. The embedded component 22 is booted-up and at step 60 the embedded component 22 runs the POST 26. The POST 26 gathers diagnostic data relating to whether the nonvolatile memory 24 has one or more memory errors. The one or more memory errors can be bit errors, alterations, or corruptions, and as described, are often caused by sterilization of the end effector 16.

In some embodiments, the POST 26 calculates a checksum value of the nonvolatile memory 24 (see step 61). The checksum is a value used to verify integrity of the nonvolatile memory 24. The checksum value is calculated using a checksum function. The checksum function can be a parity byte or parity word algorithm, a modular sum algorithm, a position-dependent checksum algorithm, or any other suitable algorithm for verifying integrity of the nonvolatile memory 24.

In one embodiment, the POST 26 calculates a past checksum value of the nonvolatile memory 24. The past checksum value is the value at the time of a prior (or previous) execution of the POST 26. The prior checksum value may be stored in the memory component 28 of the embedded component 22. The POST 26 then calculates a current checksum value of the nonvolatile memory 24. The current checksum value is the value at the time of a current execution of the POST 26. The current checksum value may also be stored in the memory component 28 of the embedded component 22. The POST 26 then compares the current checksum value to the prior checksum value of the nonvolatile memory 24. If the current checksum value is different from the prior checksum value, an error is present.

In some embodiments, the POST 26 may make this error determination based on the checksum values. Alternatively, the POST 26 may simply gather such diagnostic information without making any determinations and transmit the same to the host controller 30 (or result evaluator 38) for analysis and determination of the error. In other embodiments, both the embedded component 22 (e.g., POST 26) and the host controller 30 (e.g., the result evaluator 38) may identify the error and/or determine whether the error exists.

At step 62 the embedded component 22 reports the result of the POST 26 to the host controller 30. If the result of the POST 26 is merely (pre-analyzed) diagnostic information, the result of the POST 26 may not indicate that the error has occurred. Instead, the host controller 30 makes such determination. For example, in one embodiment, the result of the POST 26 is the current checksum value. However, in this example, the prior checksum value is stored on the host memory 34, rather than the memory component 28 of the embedded component 22. As such, the determination about whether the error has occurred is made by the host controller 30 rather than the POST 26 of the embedded component 22. Alternatively, if the result of the POST 26 includes determinations about whether the error occurred, then the reported result will indicate to the host controller 30 whether the error has occurred.

At step 64, the embedded component 22 (e.g., the POST 26) determines whether the nonvolatile memory 24 has one or more errors based on the outcome of the POST 26. If the result of the POST 26 identifies that the nonvolatile memory 24 has one or more errors, the embedded component 22 initiates step 66, described below. On the other hand, if the result of the POST 26 identifies that the nonvolatile memory 24 does not have one or more errors, the embedded component 22 performs normal processes at step 68. Normal processes include any process outside of the steps of method 40b such as, but not limited to, controlling the end effector 16, interfacing with the host controller 30 to perform post-boot processes, and the like.

At step 66 the embedded component 22 sets a fault flag. The fault flag is a memory location that if set to a particular value, conventionally either 1 or 0, indicates that a memory error has occurred. The fault flag may be stored in the memory component 28 of the embedded component 22 or in the nonvolatile memory 24 itself.

After setting the fault flag, the embedded component 22 stops functioning of any normal processes to avoid malfunction. Thereafter, the embedded component 22 waits to be reprogrammed by the host controller 30 at step 70. After the nonvolatile memory 24 is reprogrammed, the host controller 30 then reboots the embedded component 22 to effectuate the corrections to the nonvolatile memory 24. After rebooting, the method 40b is restarted and the POST 26 may be re-performed depending upon a triggering event, such as reconnection of the end effector 16, rebooting of the surgical system 10, or according to a routine maintenance check schedule (e.g., depending on frequency or duration of use of the end effector 16), and the like.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

The invention claimed is:

1. A method for correcting an error of a nonvolatile memory of an embedded component for an end effector of a robotic surgical system, the robotic surgical system including a host controller in communication with the embedded component, said method comprising the steps of:
    performing, with the embedded component of the end effector, a test process to test the nonvolatile memory;
    requesting, with the host controller of the robotic surgical system, a result of the test process from the embedded component of the end effector;
    determining, with the host controller, that the error of the nonvolatile memory has occurred after requesting the result of the test process from the embedded component by evaluating the result of the test process if received from the embedded component or by determining that the result of the test process was not received from the embedded component; and
    correcting the error of the nonvolatile memory, with the host controller, by commanding a reprogramming of the embedded component and rebooting the embedded component after reprogramming.

2. The method of claim 1 wherein performing the test process further includes the embedded component of the end effector calculating a current checksum value of the nonvolatile memory.

3. The method of claim 2 wherein performing the test process further includes the embedded component of the end effector comparing the current checksum value to a prior calculated checksum value of the nonvolatile memory and determining that the current checksum value is different from the prior calculated checksum value.

4. The method of claim 3 wherein determining that the error has occurred is further defined as the host controller of the robotic surgical system evaluating the determination that the current checksum value is different from the prior calculated checksum value.

5. The method of claim 1 further comprising starting a timeout counter with the host controller of the robotic surgical system and determining whether the result of the test process is received from the embedded component of the end effector within a predetermined amount of time lapsing after starting the timeout counter.

6. The method of claim 5 wherein determining that the result of the test process was not received is further defined as the host controller of the robotic surgical system determining that the result of the test process was not received by the host controller within the predetermined amount of time.

7. The method of claim 1 wherein performing the test process with the embedded component of the end effector occurs automatically after booting up of the embedded component.

8. The method of claim 1 wherein correcting the error is further defined as the host controller automatically rewriting at least a portion of the nonvolatile memory.

9. The method of claim 8 further comprising:
    storing, with the host controller, a copy of data from the nonvolatile memory in a host memory; and
    wherein the host controller automatically rewriting at least the portion of the nonvolatile memory further comprises copying the data to the nonvolatile memory.

10. A host controller of a robotic surgical system being configured to communicate with an embedded component of an end effector used in of the robotic surgical system and with the embedded component comprising a nonvolatile memory, and with said host controller being configured to:

request a result of a test process related to the nonvolatile memory from the embedded component of the end effector;

determine that an error has occurred in the nonvolatile memory of the embedded component after requesting the result of the test process by evaluating the result of the test process if received from the embedded component or by determining that the result of the test process was not received from the embedded component; and correct the error of the nonvolatile memory by commanding a reprogramming of the embedded component and rebooting of the embedded component after reprogramming.

11. The host controller of claim 10 further being configured to start a timeout counter and determine that the result of the test process was not received from the embedded component of the end effector within a predetermined amount of time lapsing after starting the timeout counter.

12. The host controller of claim 10 further being configured to correct the error by automatically rewriting at least a portion of the nonvolatile memory of the embedded component of the end effector.

13. The host controller of claim 12 further being configured to:

store a copy of data from the nonvolatile memory in a host memory; and automatically rewrite at least the portion of the nonvolatile memory by copying the data to the nonvolatile memory.

14. An end effector for a robotic surgical system and being configured to communicate with a host controller of the robotic surgical system, said end effector comprising an embedded component comprising a nonvolatile memory and with the embedded component being configured to:

perform a test process to test the nonvolatile memory;

report a result of the test process to the host controller of the robotic surgical system; and receive and execute a command from the host controller to reprogram the embedded component and to reboot the embedded component after reprogramming to correct an error in the nonvolatile memory determined based on the result of the test process.

15. The end effector of claim 14 wherein the embedded component is further configured to perform the test process by calculating a current checksum value of the nonvolatile memory.

16. The end effector of claim 15 wherein the embedded component is further configured to perform the test process by comparing the current checksum value to a prior calculated checksum value of the nonvolatile memory and by determining that the current checksum value is different from the prior calculated checksum value.

17. The end effector of claim 14 wherein the embedded component is further configured to reprogram by allowing the host controller to automatically rewrite at least a portion of the nonvolatile memory.

18. The end effector of claim 17 wherein the embedded component is further configured to allow the host controller to automatically rewrite at least the portion of the nonvolatile memory by allowing the host controller to write data to the nonvolatile memory, the data being a copy of data previously stored on the nonvolatile memory.

* * * * *